United States Patent [19]

Fini et al.

[11] Patent Number: 4,736,636
[45] Date of Patent: Apr. 12, 1988

[54] DEVICE FOR SELECTIVELY SAMPLING FLUID FROM TWO SECTIONS OF A LINE

[75] Inventors: Massimo Fini, Mirandola; Pietro Vescovini, Medolla, both of Italy

[73] Assignee: Dideco S.p.A., Mirandola, Italy

[21] Appl. No.: 886,789

[22] Filed: Jul. 18, 1986

[30] Foreign Application Priority Data

Jul. 18, 1985 [IT] Italy ............................... 21621 A/85

[51] Int. Cl.$^4$ ........................ G01N 1/10; G01N 1/14
[52] U.S. Cl. .............................. 73/863.73; 73/863.85
[58] Field of Search ............. 73/863.73, 863.85, 863.86

[56] References Cited

U.S. PATENT DOCUMENTS

| | | | |
|---|---|---|---|
| 2,864,254 | 12/1958 | McDonald et al. | 73/863.73 |
| 3,353,411 | 11/1967 | Nodeua et al. | 73/863.85 |
| 3,884,082 | 5/1975 | Merciadis | 73/863.73 |
| 4,476,731 | 10/1984 | Chorney et al. | 73/863.73 |
| 4,577,515 | 3/1986 | Someya et al. | 73/863.73 |

Primary Examiner—Tom Noland
Attorney, Agent, or Firm—Neuman, Williams, Anderson & Olson

[57] ABSTRACT

The technical field dealt with is that of fluid conveyance, and the invention relates to a device for selectively sampling fluid from two sections of a line which ensures great operating practicality and minimal dimensions. The solution consists of a device comprising a selecting element with a cavity associable with a syringe and comprising an appendix suitable for rotating in a seat of a fixed element to which converge three conduits, the two end conduits being connectable with the two parts of the line and the central conduit being connectable with a drain, said selecting element having two passages, each of which is suitable for establishing a communication between one of the end conduits and the central conduit, and a third intermediate passage suitable for establishing a communication selectively between the two end conduits and said cavity.

7 Claims, 2 Drawing Sheets

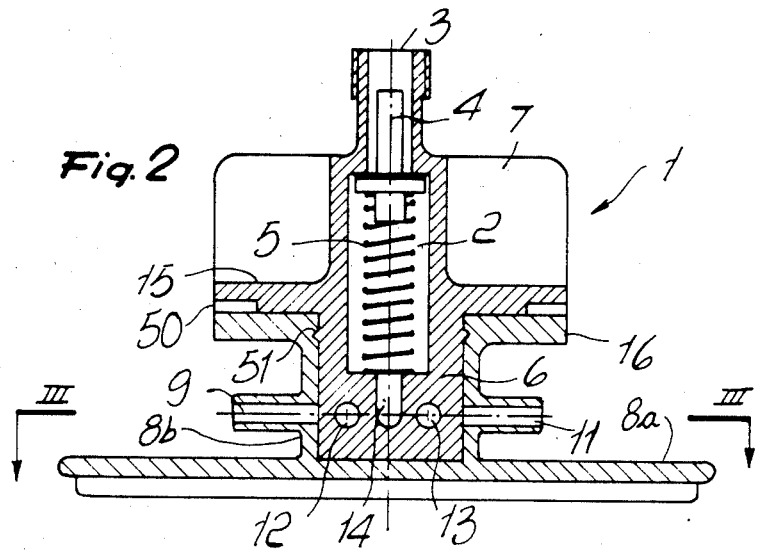
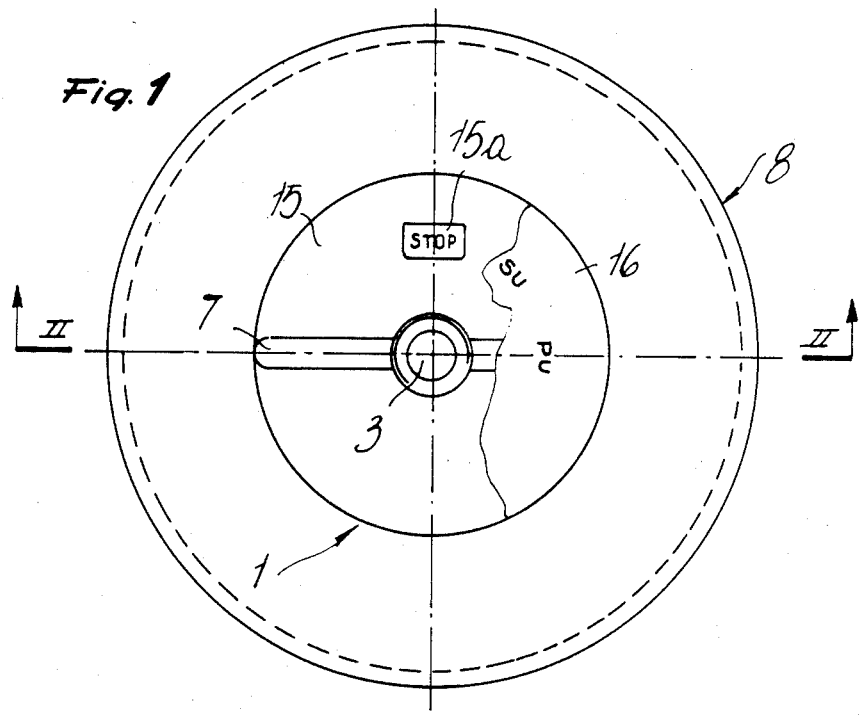

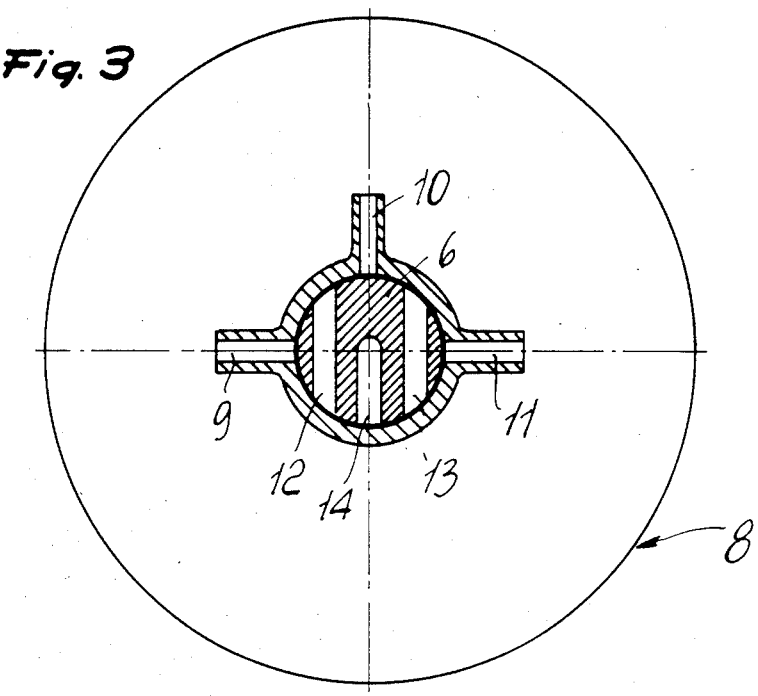
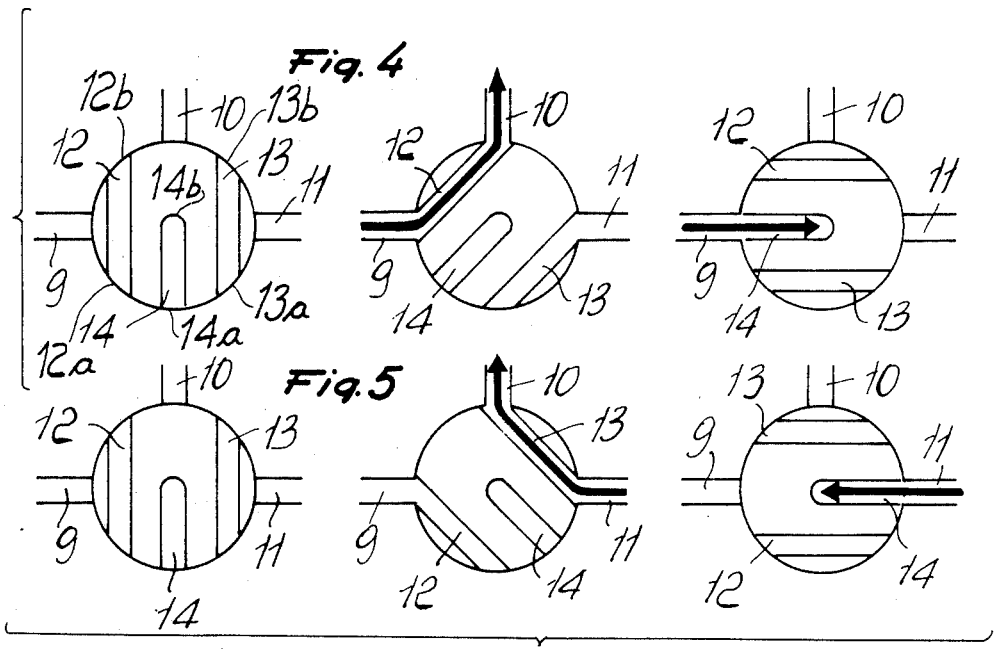

4,736,636

DEVICE FOR SELECTIVELY SAMPLING FLUID FROM TWO SECTIONS OF A LINE

BACKGROUND OF THE INVENTION

The invention relates to a device for selectively sampling fluid from two sections of a fluid conveying line.

It is known that in many fields of activity it is necessary to remove samples from two sections of a fluid conveyance line, such as, for example, the input and output sections of an apparatus, for controlling the changes effected on the fluid in passing through the apparatus itself.

This occurs, for example, in the field of extracorporeal blood circulation, when it is required to perform samplings of the blood at the input and at the output of an oxygenating apparatus.

The devices currently in use, formed for example by three-way taps coupled in series, have some disadvantageous characteristics, essentially constituted by large bulk and complicated operation, with operating modes which are frequently anything but evident.

SUMMARY OF THE INVENTION

The aim of the present invention is to provide a device having small bulk and great operating simplicity.

The aim proposed, as well as objects which will become apparent hereinafter, are achieved by a device for selectively sampling fluid from two sections of a line, according to the invention, characterized in that it comprises a selecting element having an axial cavity, opening to the outside at an end intended for being associated with a syringe, and comprising a cylindrical appendix suitable for rotating, in consequence of a manual action on gripping elements, in a seat provided in a fixed element to which three conduits converge, the two end conduits being suitable for being connected respectively with the two sections of the line and the central conduit with a drain, said selecting element having two passages, each of which is suitable for establishing a communication between one of the end conduits and the central conduit, and a third passage in an intermediate position, suitable for establishing a communication selectively between the two end conduits and said axial cavity.

BRIEF DESCRIPTION OF THE DRAWINGS

Further features and advantages will become better apparent from the description of a preferred, but not exclusive, embodiment of the invention, illustrated by way of non-limitative example only in the accompanying drawings, where:

FIG. 1 is a top view of the invention intended for sampling on the input and output lines of an apparatus for treating blood in extracorporeal circulation, with removed a part of the selecting element, which is in closed position;

FIG. 2 is a cross sectional view along the plane II—II of FIG. 1;

FIG. 3 is a cross sectional view along the plane III—III of FIG. 2;

FIG. 4 shows the sequence of operations for sampling the output of the apparatus;

FIG. 5 illustrates the sequence of operations for sampling the input of the apparatus.

DESCRIPTION OF THE PREFERRED EMBODIMENT

With reference to the above figures, at 1 is generally indicated the selecting element, which has the axial cavity 2, open to the outside at the end 3, through which a sampling syringe can be introduced, by lowering the shutter 4 against the bias of the spring 5.

The selecting element 1 comprises the cylindrical appendix 6 suitable for rotating, in consequence of an operator acting on the gripping fins 7, inside a seat provided within the fixed element generally indicated at 8 and having a base plate 8a formation and a boss formation 8b projecting from the base plate formation 8a, to which three conduits or connectors converge, angularly spaced apart from each other by 90°: the conduit 9 is intended to be connected with the output line of the apparatus, the conduit 10 with a drain or dump and the conduit 11 with the input line of the apparatus.

The appendix 6 comprises the two passages 12 and 13, suitable for establishing a communication between the conduit 10 and respectively the conduits 9 and 11, symmetrically arranged relatively to a plane passing through the rotation axis containing a third L-shaped passage 14, suitable for establishing a selective communication between the two conduits 9, 11 and the cavity 2, all of which will be better explained in the description of the operation. Note that passage 12 has an inlet opening 12a and an outlet opening 12b, passage 13 has an inlet opening 13a and an outlet opening 13b and passage 14 has an inlet opening 14a and an outlet aperture 14b (FIG. 4).

Rigidly coupled with the selecting element 1 is the disk 15, having a small port 15a suitable for allowing the reading of indications placed on the underlying disk 16, rigidly coupled with the fixed element 1 at the operating positions of said selecting element: thus, as an example, in the situation depicted in FIGS. 1, 2 and 3, through the small port 15a the indication STOP is read, since the device is in closed position, but by rotating the element 1 through 45° clockwise, the indication SU will be read, which indicates "output drain", and by again rotating through 45°, the indication PU will be read, which indicates "output sampling".

Abutments or reference elements 50 (FIG. 2) symbolically illustrate means suitable for stopping the selecting element in the operating positions, and a limiter 51 symbolically illustrated in FIG. 2 prevents rotations greater than 90° in the two directions from the position shown in FIGS. 1, 2 and 3, complete the device.

The operation of the invention is extremely simple; if it is desired to perform sampling of blood from the output of the apparatus, it is sufficient to proceed according to the sequence of FIG. 4: from the closing position, the selecting element 1 is rotated clockwise through 45°, so that the passage 12 establishes a communication between the conduit 9, which is connected with the output line of the device, and the conduit 10 to allow draining of a certain amount of blood, then said element 1 is rotated through additional 45° so as to establish a communication between the passage 14 and the conduit 9, to allow blood to access the cavity 2 from which sampling is performed by means of a syringe.

FIG. 5 shows the sequence of operations for performing sampling of blood from the input of the apparatus: from closing position, the selecting element is rotated anticlockwise through 45°, so that the passage 13 establishes a communication between the drain 10 and the conduit 11, which is connected with the input line and, after some time, the selecting element is rotated through additional 45°, so as to establish a communication between the passage 14 and the conduit 11, consequently allowing blood to access the cavity 2.

From what has been described, it is seen that the invention provides an extremely simple structure with very small bulk, and that the operating modes are immediately perceivable due to their intrinsic simplicity and to the indications which can be read in the different phases.

The invention described is susceptible to numerous modifications and variations, all of which are comprised within the scope of the invention concept: thus, as an example, the conduits which converge to the seat on the fixed element can be separated by angles different from 90°, and consequently the shape of the passages of the selecting element will be dieferent.

In the practical implementation of the invention, all the elements may be replaced with other technically equivalent elements: furthermore, any materials, dimensions and shapes may be employed.

We claim:

1. Device for selectively sampling fluid from two sections of a fluid conveying line, said device comprising a fixed element having a cylindrical seat, two external conduits and a central conduit, each of said external two and said central conduits converging into said seat, said seat defining an axis of rotation; a selecting element having an axial cavity opening on the outside at an end intended to be associated with a syringe, and a cylindrical appendix inserted into said seat and suitable for rotating therein about said rotation axis, in consequence of a manual actuation on gripping elements; said three conduits being suitable to be connected, said two external conduits respectively with the two sections of the line and said central conduit with a drain; said selecting element having two passages, each suitable for establishing alternatively a communication between one of said two external conduits and said central conduit, and a third passage in an intermediate position suitable for establishing a communication selectively between said two external conduits and said axial cavity, thereby to fill said axial cavity with a fluid sample conveyed thereto through said third passage from one of the two sections of the line and alternatively from the other of the two sections of the line, and alternatively to drain said fluid from the one section of the line through one of said two passages and to drain said fluid from the other of the two sections of the line through the other of said two passages, upon selected angular rotations of said selecting element about said axis of rotation.

2. Device according to claim 1, wherein said three conduits converging to said seat of said fixed element are angularly spaced apart from each other by 90°, each of said two passages is suitable for establishing a communication between only one of said two external conduits and said central conduit, symmetrically arranged with respect to a plane containing said rotation axis and extending transverse to said rotation axis, and said third passage contained in the plane of symmetry of said two passages and having one end thereof opening into said axial cavity and having another end thereof, said third passage being suitable for selectively establishing communication through said other end thereof between said two conduits and said axial cavity upon selected angular rotation of said selecting element.

3. Device according to claim 1, wherein with the selecting element is rigidly coupled a disk, having a small port suitable for allowing reading of indications placed on a underlying disk, rigidly coupled with the fixed element at the operating positions of said selection element.

4. Device according to claim 1, further comprising a spring shutter in the axial cavity of the selecting element, suitable for being put in an opening position by the action of the syringe which is inserted for sampling.

5. Device according to claim 1, further comprising abutments suitable for stopping the selecting element in operating positions.

6. Device according to claim 1, further comprising a limiter suitable for preventing a rotation of said selecting element such as to establish a communication between said third passage and said central conduit.

7. A device for selectively sampling fluid from two sections of a fluid conveying line, said device comprising:
a fixed element having a base plate formation, a boss formation projecting from said base plate formation and internally defining a cylindrical seat and an axis of rotation extending transverse to said base plate formation, a first connector formation opening into said seat and radially outwardly extending therefrom for connection with a first section of said fluid conveying line, a second connector formation opening into said seat and radially outwardly extending from said seat at an angle with respect to said first connector formation for connection with a second section of said fluid conveying line and a third connector formation opening into said seat and radially outwardly extending from said seat at an angle with respect to said first and said second connector formations for connection with drain means,
a rotatable selecting element having a body portion with an axial cavity and a cylindrical appendix defining a peripheral surface and rotatably supported within said seat about said axis of rotation thereof, a first passage in said cylindrical appendix and having a first inlet opening at a peripheral surface thereof and a first outlet opening at said peripheral surface at a distance from said first inlet opening, a second passage in said cylindrical appendix and having a second inlet opening at said peripheral surface and a second outlet opening at said peripheral surface at a distance from said first and second inlet openings and at a distance from said first outlet opening, and a third passage having a third inlet opening at said peripheral surface at a distance from said first and second inlet openings and at a distance from said first and second outlet openings, said third passage having a third outlet aperture permanently opening into said axial cavity, said axial cavity having an outwardly facing aperture and yieldable shutter means for cooperation with a sampling syringe,
said rotatable selecting element being suitable, upon selected angular rotations thereof, for selectively establishing alternatively a first communication between said first connection formation and said axial cavity, a second communication between said second connector formation and said axial cavity, a third communication directly between said first and third connector formations and a fourth communication directly between said second and third connector formations by means of one of said first, second and third passages at a time.

* * * * *